United States Patent
Kalbermatten

(10) Patent No.: US 6,820,498 B2
(45) Date of Patent: Nov. 23, 2004

(54) APPARATUS FOR ORIENTING TABLETS

(75) Inventor: Gilles Kalbermatten, Rosenau (FR)

(73) Assignee: Sotax Aktiengesellschaft, Allschwil (CH)

( * ) Notice: Subject to any disclaimer, the term of this patent is extended or adjusted under 35 U.S.C. 154(b) by 0 days.

(21) Appl. No.: 10/430,104

(22) Filed: May 6, 2003

(65) Prior Publication Data

US 2003/0209098 A1 Nov. 13, 2003

(30) Foreign Application Priority Data

May 7, 2002 (CH) .................................... 2002 0770/02

(51) Int. Cl.$^7$ ........................... G01N 3/40; G01N 33/15
(52) U.S. Cl. .............................. 73/856; 73/866; 73/12; 73/788
(58) Field of Search ............................ 73/12.01, 12.09, 73/78, 81, 82, 87, 781, 788–791, 799, 818, 821, 824, 856, 866

(56) References Cited

U.S. PATENT DOCUMENTS

| | | | | |
|---|---|---|---|---|
| 2,041,869 A | * | 5/1936 | Smith et al. ................... 73/821 |
| 2,645,936 A | * | 7/1953 | Albrecht ....................... 73/821 |
| 2,975,630 A | * | 3/1961 | Michel ........................... 73/78 |
| 3,630,073 A | * | 12/1971 | Michel ......................... 73/818 |
| 3,757,566 A | * | 9/1973 | Flury ........................... 73/821 |
| 3,811,552 A | * | 5/1974 | Wagers et al. .............. 198/393 |
| 3,905,472 A | * | 9/1975 | Schuster ...................... 198/835 |
| 3,943,757 A | * | 3/1976 | Wilhelm, Jr. ................... 73/78 |
| 4,022,056 A | * | 5/1977 | Barland .......................... 73/78 |
| 4,054,050 A | * | 10/1977 | Reid ............................ 73/806 |
| 4,061,788 A | * | 12/1977 | Wommack ................... 426/248 |
| 4,472,960 A | * | 9/1984 | Motoyama et al. ............... 73/7 |
| 4,542,646 A | * | 9/1985 | Smith et al. ................... 73/78 |
| 4,641,534 A | * | 2/1987 | Schneider et al. ............ 73/856 |
| 4,848,162 A | * | 7/1989 | Metcalfe et al. .............. 73/824 |
| 4,957,003 A | * | 9/1990 | Hiestand et al. .............. 73/818 |
| 5,555,768 A | * | 9/1996 | Shaffer et al. ............. 73/865.8 |
| 6,079,284 A | * | 6/2000 | Yamamoto et al. ......... 73/865.8 |
| 6,257,079 B1 | * | 7/2001 | Mueller ........................ 73/866 |
| 6,260,419 B1 | * | 7/2001 | Kramer ........................ 73/821 |

FOREIGN PATENT DOCUMENTS

JP          57160816 A   * 10/1982   ........... B65G/47/14

* cited by examiner

*Primary Examiner*—Helen Kwok
*Assistant Examiner*—David A. Rogers
(74) *Attorney, Agent, or Firm*—Sidley Austin Brown & Wood, LLP

(57) ABSTRACT

An apparatus for orienting tablets on a measuring station includes a horizontal transfer table, two rollers provided in the support plane of the transfer table and arranged parallel side by side, with the upper generators of the rollers being flush with the support surface or projecting slightly beyond it, and a drive device for driving the two rollers in opposite directions so that a test tablet transferred onto the two rollers is automatically oriented according to the axes of the two rollers; and a tablet tester including the apparatus.

5 Claims, 2 Drawing Sheets

APPARATUS FOR ORIENTING TABLETS

BACKGROUND OF THE INVENTION

1. Field of the Invention

The invention relates to an apparatus for orienting tablets, in particular oblong tablets and other nonuniform tablets, in tablet testers.

Tablet testers are used predominantly in the pharmaceutical industry and also in science and research for quality control and product characterization.

In the development and particularly in the routine quality control of solid dosage forms, the determinations of weight, thickness, length and hardness are of major importance. For this reason, various testers which allow the determination of these physical parameters by means of a plurality of measuring stations have already been developed.

In the case of known testers, the tablets pass from a feed means onto a transport means with a rake having a plurality of forks which further transport the tablets on a conveyor belt. A movement means for the rake transports the rake over a distance in the transport direction, then raises the rake and guides it in the raised state against the transport direction over a corresponding distance back again. The rake is then lowered and is moved again over a transport distance. Furthermore, a plurality of test stations, namely a balance, a test station for the thickness measurement and a test station for the fracture test are provided along the movement path of the rake. Most tablet testers are suitable for round or spherical tablets but less so for oblong tablets and similarly shaped test specimens which have a substantially oval shape in plan view, a flat wall along their circumference and a curve top and bottom. Such test specimens give rise to considerable difficulties on these apparatuses. They cannot in fact always be optimally oriented in the required manner in the various test stations and especially in the station for testing the ultimate strength.

2. Description of the Prior Art

A tablet tester which is suitable for positioning oblong tablets or similarly shaped test specimens in measuring stations of a tester is described in German Patent 197 33 436. The tablet tester disclosed therein is distinguished by a feed means for feeding individual test specimens to a balance whose balance pan has a base which is inclined in the transport direction and is in the form of a channel. A transport means below the balance pan, on which the test specimens are placed from the balance pan with their longitudinal axis parallel to the longitudinal direction of the channel, transports the test specimen in this orientation to the test stations.

This known apparatus, too, does not solve the problem of the horizontal orientation and positioning of the test tablets without disadvantages. Thus, this apparatus does not permit optimal orientation of the test specimen directly at the measuring station, which, for example, serves for the hardness test, repeatedly resulting in incorrect measurements and faults of the tester.

The hardness of a test specimen is usually measured in a high-resolution load cell which has a stationary stop and a movable press jaw. The test specimen is transported on a guide track between stop and press jaw, the test specimen preferably touching the stop. The press jaw is then moved by means of a stepping motor toward the stop and the test specimen in front of it. The force exerted by the press jaw with each step of the motor is measured and recorded and is constant and very small as long as the stop does not touch the test specimen or the latter is moved without opposing pressure over the guide track. If the press jaw presses the test specimen against the stop, the force exerted by it increases with each step of the stepping motor until the test specimen breaks. The force applied for this purpose is recorded and serves as a measure of hardness of the test specimen. The sudden decline in the force applied by the press jaw on breaking of the test specimen furthermore serves as a termination condition for ending the measurement. The press jaw is moved back to its starting position and the next test specimen can be tested.

In a tester used especially for the hardness test and disclosed in German Patent 100 24 970, the feed movement of the movable press jaw for transporting the test specimen in the direction of the stationary stop is continuously interrupted, with carrying of the test specimen, and the press jaw is drawn back and advanced, the feed and withdrawal movement of the press jaw being small in relation to its total feed distance relative to the stop, so that the test specimen preferably guided in channel swings back into its rest position and the press jaw then begins to push again in the direction of the stop until the test specimen has reached the stop. Although this method makes it possible to carry out a hardness test on a test specimen which has at least one curved main surface, it does not permit trouble-free measurement of oblong tablets.

SUMMARY OF THE INVENTION

It is the object of the present invention to provide a novel apparatus which permits manual, semiautomatic or automatic orientation of tablets introduced into a measuring station of a tablet tester, in which the measurement can be controlled with sufficient accuracy and can be repeated at relatively short time intervals with new test tablets, and which at the same time does not have the disadvantages of orientation means used in known testers.

This object is achieved by an apparatus which comprises
a preferably horizontal transfer table,
two rollers provided in the support plane of the transfer table and arranged parallel side by side, the upper generators of the rollers being flush with said support surface or projecting slightly beyond it, and
a drive device which, on operation of the apparatus, drives the two rollers in opposite directions so that the left roller is rotated clockwise and the right roller counterclockwise, so that a test tablet transferred onto the two rollers is automatically oriented according to the axes of the two rollers.

The present invention also relates to a tablet tester.

The apparatus according to the invention and the tester according to the invention have various advantages in comparison with the prior art. Thus, the invention has the advantage that in particular oblong tablets are oriented absolutely accurately and automatically along their own body length axis as soon as they come to rest on the pair of rollers of the apparatus according to the invention, without the use of horizontal orientation elements, and that, owing to the lack of movable mechanical elements, the horizontal rollers which serve for orientation are not very susceptible to faults. The apparatus according to the invention and the tester according to the invention are therefore also particularly suitable for use in automatic, semiautomatic or manual hardness testing of tablets having a particle length of, for example, 5 mm to 20 mm and a mean particle width of, usually, 4 mm to 8 mm.

BRIEF DESCRIPTION OF THE DRAWINGS

Embodiments of the invention are described below with reference to drawings. In the drawings.

DESCRIPTION OF THE PREFERRED EMBODIMENTS

Figure 1:
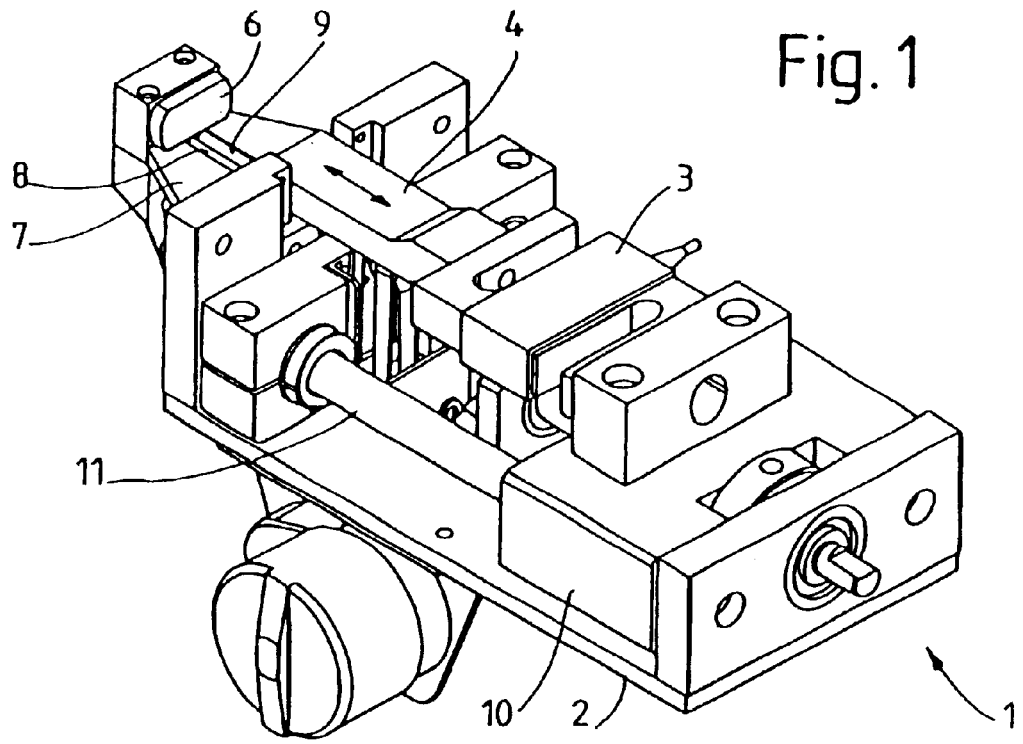
FIG. 1 shows a perspective partial view of a tablet tester comprising an apparatus for orienting test tablets.
Figure 2:
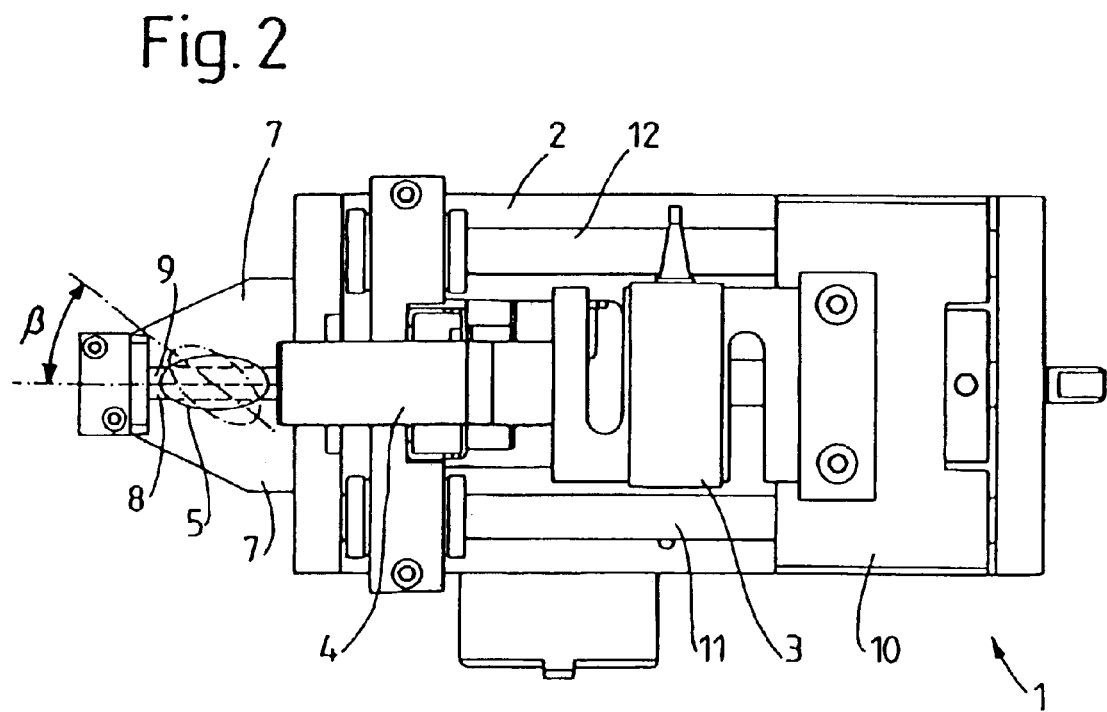
FIG. 2 shows a plan view of the apparatus according to FIG. 1.
Figure 3:
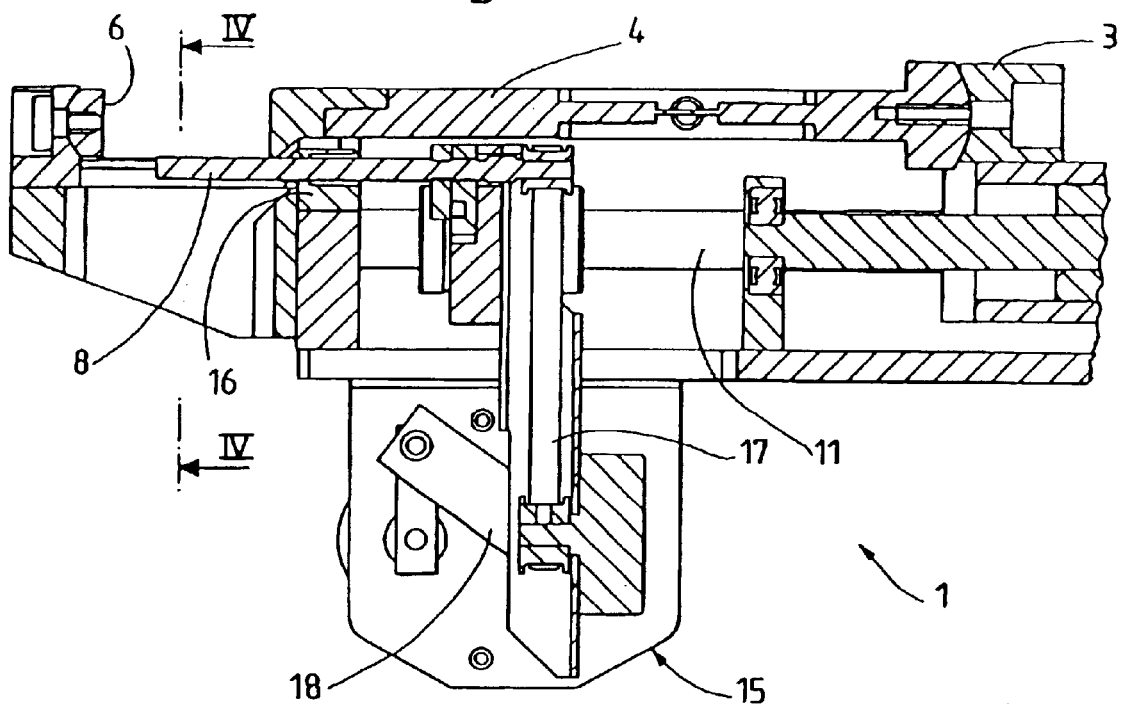
FIG. 3 shows a longitudinal section through a part of the tablet tester and FIG. 4 shows a section along the line IV—IV of FIG. 3.
Figure 4:
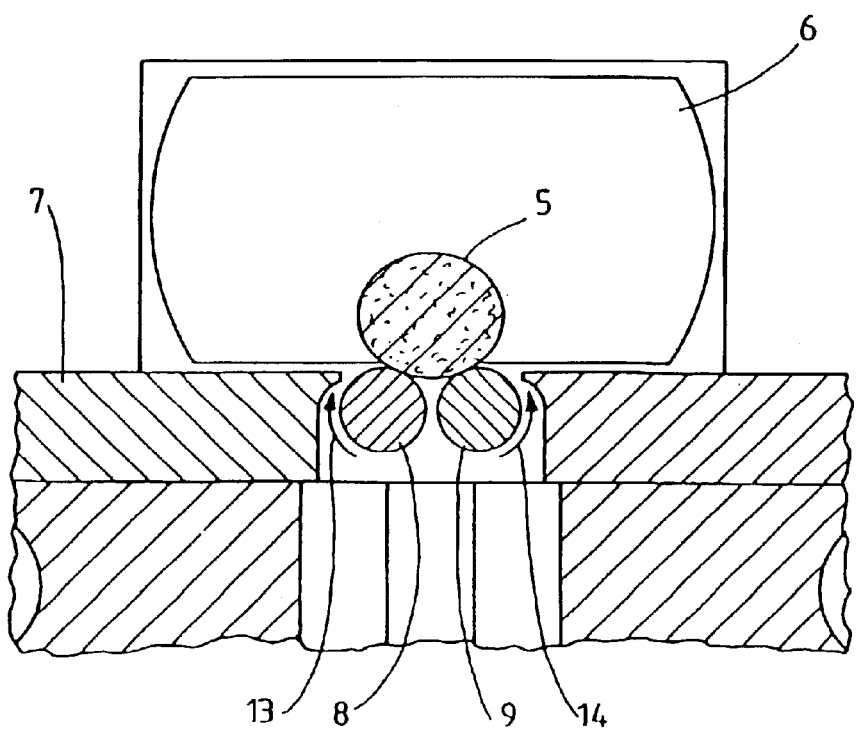

The head part of a tablet tester, shown in part in FIGS. 1 to 3 and denoted as a whole by 1 has a load cell 3 arranged on a horizontal baseplate 2. This is a known design and has a ram 4 for breaking the tablet 5 to be tested for which purpose a tablet stop 6 is additionally coordinated with the ram 4.

In the plane which is provided between stop 6 and ram 4 and which is formed by a preferably horizontal transfer table 7 serving for tablet transport, according to the invention two rollers 8 and 9 arranged parallel side by side are provided for orienting the test tablet 5. The rollers 8 and 9 are in particular aligned parallel to the impact direction of the ram 4, and the longitudinal axis of the ram 4 is in a vertical plane present exactly between the two rollers 8 and 9.

The upper generators of the two preferably metallic rollers 8 and 9 are flush with the support surface of the transfer table 7 or project slightly beyond it.

The rollers 8 and 9 each have, for example, a diameter of 3 mm to 5 mm, preferably 4 mm and a distance between axes of 3.5 mm to 6 mm, preferably 4.4 mm. They are moreover connected to a drive device 10 and are driven in opposite directions by means of shafts 11 and 12 in the direction of the arrow 13 or 14, respectively, so that the left roller is rotated clockwise and the right roller counterclockwise.

If a test tablet 5, for example an oblong tablet, now travels from the transfer table 7 onto the two rotating rollers 8 and 9, said tablet is oriented automatically through the angle β according to the axes of the two rollers 8 and 9, i.e. the body length axis is oriented according to the two roller axes, and this is done regardless of its original position relative to the roller axes. According to the invention, the tablet 5 can thus be oriented relatively simply and without horizontally movable elements along a specific axis and can thus be subjected in an optimum position to the subsequent hardness test which has already been described at the outset and will not be discussed in more detail below.

In the section shown in FIG. 3, the pairs 8 and 9 of rollers are shown slightly set back compared with the operating state. These are in fact additionally horizontally displaceable by means of a further drive device 15, so that they can be passed through scraping means 16, for example for cleaning purposes. The movement can be effected by drive means 17 and 18 in such a way that said movement is nonuniform, i.e. begins slowly on travelling back, then becomes faster, has the highest speed in the completely retracted position and decreases continuously in speed again during forward displacement. Particularly when the pairs 8 and 9 of rollers are travelling back, the tablet fragments fall down vertically from the transfer table 7 into a waste container which is not shown so that the plane of the transfer table 7 is thus automatically cleaned.

Moreover, the apparatus according to the invention is by no means restricted to applications for the hardness testing of pharmaceutical tablets. Testers for testing other solid products, such as detergent or fertilizer tablets can also readily be equipped with the apparatus according to the invention for the orientation of test specimens and/or, instead of a load cell for the hardness determination or in addition thereto, the tester can be provided with measuring means for determining the length, weight and mean width of a test specimen.

What is claimed is:

1. An apparatus for orienting tablets on a measuring station of a tablet tester, which comprises a preferably horizontal transfer table, two rollers provided in the support plane of the transfer table and arranged parallel side by side, the upper generators of the rollers being flush with said support surface or projecting slightly beyond it, and a drive device which, on operation of the apparatus, drives the two rollers in opposite directions so that the left roller is rotated clockwise and the right roller counterclockwise, so that a test tablet transferred onto the two rollers is automatically oriented according to the axes of the two rollers.

2. The apparatus as claimed in claim 1, wherein the two rollers consist of metallic material and each have a diameter of 3 mm to 5 mm, preferably 4 mm, and a distance between axes of 3.5 mm to 6 mm, preferably 4.4 mm.

3. The apparatus as claimed in claim 1, wherein the two rollers are horizontally displaceable and wherein scraping means are present, through which the rollers are passed during horizontal displacement.

4. A tablet tester, comprising:

at least one measuring station for determining at least one physical parameter of a test tablet, and an apparatus for orienting tablets on a measuring station and including:

a preferably horizontal transfer table, two rollers provided in the support plane of the transfer table and arranged parallel side by side, the upper generators of the rollers being flush with said support surface or projecting slightly beyond it, and a drive device which, on operation of the apparatus, drives the two rollers in opposite directions so that the left roller is rotated clockwise and the right roller counterclockwise, so that a test tablet transferred onto the two rollers is automatically oriented according to the axes of the two rollers.

5. The tablet tester as claimed in claim 4 wherein said tablet tester possesses a load cell which serves for determining the hardness and has a ram for breaking the tablet to be tested and a tablet stop opposite the ram, wherein the two rollers arranged parallel side by side are provided in a plane provided between stop and ram, the longitudinal axis of the ram being in a vertical plane present exactly between the two rollers.

* * * * *